US005782892A

United States Patent [19]
Castle et al.

[11] Patent Number: 5,782,892
[45] Date of Patent: Jul. 21, 1998

[54] MEDICAL LEAD ADAPTOR FOR EXTERNAL MEDICAL DEVICE

[75] Inventors: Vernon P. Castle, Bloomington; Jerrold Nelson, Fridley; George W. Gullickson, Bloomington; Frank L. Skubitz, Andover, all of Minn.

[73] Assignee: Medtronic, Inc., Minneapolis, Minn.

[21] Appl. No.: 843,084

[22] Filed: Apr. 25, 1997

[51] Int. Cl.$^6$ .................................................. A61N 1/372
[52] U.S. Cl. .............................. 607/37; 439/909; 607/10
[58] Field of Search ...................... 439/909; 607/37, 607/115, 116, 119, 122, 10; 600/372, 373, 374, 377; 29/592.1

[56] References Cited

U.S. PATENT DOCUMENTS

| 4,226,244 | 10/1980 | Coury et al. ................. 607/37 |
| 4,245,642 | 1/1981 | Skubitz et al. .............. 128/419 P |
| 4,341,226 | 7/1982 | Peters ........................... 128/784 |
| 4,466,441 | 8/1984 | Skubitz et al. .............. 128/419 P |
| 4,545,381 | 10/1985 | Bournay, Jr. et al. ....... 128/419 P |
| 4,942,876 | 7/1990 | Gotthardt ....................... 607/37 |
| 4,944,088 | 7/1990 | Doan et al. ..................... 29/858 |
| 4,951,687 | 8/1990 | Ufford et al. ................. 128/786 |
| 5,007,435 | 4/1991 | Doan et al. ................... 128/784 |
| 5,050,602 | 9/1991 | Osypka ........................... 607/37 |

*Primary Examiner*—William E. Kamm
*Assistant Examiner*—Kennedy J. Schaetzle
*Attorney, Agent, or Firm*—Thomas F. Woods; Harold R. Patton

[57] ABSTRACT

A medical lead adaptor that provides a rapid, secure, insulated connection of the lead connector end assembly of one or more implantable cardiac lead with an external medical device is disclosed. The adaptor connector assembly is configured with an elongated bipolar receptacle to accept a bipolar, in-line, or a unipolar lead connector end having common dimensions and with connector pin and ring, bipolar receptacle contacts spaced apart from one another therein. An elongated slot that extends laterally to an adaptor connector assembly exterior surface allows the lateral insertion of a stylet wire into the elongated bipolar receptacle. A separate pair of positive and negative polarity unipolar receptacles are provided for receiving unipolar medical lead connector pins and making electrical and mechanical contact with unipolar receptacle contacts therein. First and second spaced apart contact blades are located within the receptacle housing each having one of the unipolar and bipolar receptacle contacts formed therein. The first and second contact blades are movable together from a normally closed or locked position blocking the receptacles to an open position for allowing insertion or removal of selected lead connector end assemblies into or from the bipolar and/or unipolar receptacles.

33 Claims, 6 Drawing Sheets

MEDICAL LEAD ADAPTOR FOR EXTERNAL MEDICAL DEVICE

CROSS-REFERENCE TO RELATED APPLICATIONS

Reference is hereby made to commonly assigned, co-pending U.S. patent application Ser. No. 08/846,193 filed on even date herewith, for MEDICAL LEAD ADAPTOR in the names of Thomas J. Winkler et al.

FIELD OF THE INVENTION

The present invention generally relates a medical lead adaptor for making a temporary connection between a medical lead and an external medical device, particularly for making the connection of a permanent or temporary cardiac lead or heart wire with an external cardiac monitor or stimulator, depending on the nature of the implantable cardiac lead or heart wire.

BACKGROUND OF THE INVENTION

The earliest instances of relatively prolonged cardiac stimulation, namely cardiac pacing, of a patient's heart was effected through implanted cardiac leads attached to the heart muscle at distal electrode ends and extended through an incision in the patient's skin. Initially, cardiac pacing was employed during post-operative recovery from cardiac surgery, and the attachment to the heart was made to the epicardium during the surgical procedure. To effect unipolar pacing of the heart, a single such implantable pacing lead was employed in conjunction with a subcutaneously implanted or skin surface attached return electrode coupled to an external lead conductor. To effect bipolar pacing of the heart, two such implantable pacing leads were implanted with the electrode ends implanted a distance apart. Initially, the attachment mechanism typically required a second surgical procedure to remove the distal electrode(s) and the pacing lead(s).

The attachment of the proximal ends of the lead conductors to the temporary cardiac pacemaker connector terminals was initially effected by simply stripping insulation from the proximal conductor ends, inserting the bare conductor ends around or through transverse openings in threaded posts, and tightening down thumb nuts. Later, finished connector pins were formed at the proximal connector ends of the lead bodies that could be inserted into end openings of the thumb nuts and connector posts.

Implantable pacing leads evolved into permanent, unipolar and bipolar, endocardial and epicardial, pacing leads for chronic implantation in a patient and with proximal electrical connector assemblies connected with connector terminals of a totally implanted, cardiac pacemaker pulse generator. To withstand stress, implantable pacing lead conductors were formed of coiled wire and inserted within an insulative lead body lumen, thereby providing a coiled wire lumen that was sized to receive a stiffening stylet wire to assist transvenous implantation of endocardial pacing leads. The proximal end of the coiled wire conductor was attached to a tubular connector pin at the terminus of the lead connector end shaped to be received in the connector assembly of the implantable pacemaker pulse generator. In the case of endocardial permanent pacing leads, the connector pin was formed with a lumen therein aligned with the coiled wire lumen so that the stiffening stylet wire could be inserted down the length of the lead body, used during the transvenous introduction, and withdrawn after placement of the distal electrode was achieved. Many of these features are employed in current permanent pacing leads.

More recently, bipolar and multi-polar permanently implantable pacing leads and leads for use in pacing and cardioversion/defibrillation (collectively referred to as permanent implantable cardiac leads) have been developed using coaxially arranged, coiled wire conductors and/or parallel-wound, multi-filar coiled wire conductors. In the case of endocardial cardiac leads, the stylet wire lumen is employed to receive the stiffening stylet wire for implantation as described above. The proximal connector end assemblies are formed with at least two spaced apart lead connector elements arranged in-line from a proximal lead connector pin to at least one more distally located ring-shaped element or lead connector ring. Typical bipolar in-line lead connector assemblies for multi-filar, coiled wire conductors are shown, for example, in commonly assigned U.S. Pat. Nos. 4,944,088 and 4,951,687 and 5,007,435, respectively, incorporated herein by reference.

Different manufacturers have produced implantable cardiac leads with lead connector end assemblies that match the connector block terminals of implantable medical devices of the same manufacturer. In recent years, one dimensional pacemaker connector standard has been made implemented, namely the low profile connector "IS-1" standard (ISO 5841-3:1992(E)) for bipolar in-line and unipolar lead connector end assemblies. Other permanent, bipolar, in-line, cardiac lead connector end assemblies conform dimensionally with the MEDTRONIC 3.2 mm low profile connector standard. Certain permanent unipolar cardiac lead connector end assemblies conform dimensionally with the MEDTRONIC 5 mm connector standard.

Unipolar and bipolar, temporary endocardial pacing leads and temporary epicardial heart wires were also developed for implantation of the distal electrode(s) thereof in contact with the endocardium or sutured through the epicardium of the hearts of hospitalized patients. The lead body size of these temporary pacing leads and heart wires has typically been smaller than that of permanent cardiac leads because of the absence of an internal wire coil lumen for receiving a stiffening stylet wire. Still, in the case of bipolar temporary pacing leads and heart wires, either a lead connector pin and ring set having comparable separations apart to those of permanent cardiac leads or bifurcated lead connector assemblies are employed providing a pair of lead connector pins. Exemplary temporary bipolar pacing leads include the MEDTRONIC® TEMPTRON temporary pacing leads having a uniform diameter, in-line, connector pin and ring assembly. Exemplary heart wires include the MEDTRONIC® Model Nos. 6491, 6492, 6494 and 6500 unipolar heart wires and the Model 6495 bipolar heart wire as described in commonly assigned U.S. Pat. No. 4,341,226, incorporated herein by reference.

During a hospitalization, a heart wire or temporary pacing lead of these types may be implanted to allow monitoring and demand pacing of the heart as the patient recovers from cardiac surgery or another condition. In addition, it may be necessary at times to connect the proximal connector end of a permanent cardiac lead already implanted in a patient to a temporary external pacemaker. The proximal connector end assemblies in each case are attached, for example, to external medical device connector terminals of MEDTRONIC® Model Nos. 5348 or 5388 external single chamber or dual chamber cardiac pacemakers. The external medical device connector terminals of such external cardiac pacemakers can constitute either spaced RCA type female sockets or a shielded connector receptacle that are not compatible with cardiac lead connector end assemblies.

Therefore, when a bipolar heart wire or permanent or temporary pacing lead is to be connected, it is necessary to use a further "patient cable" adaptor to complete the connection. The MEDTRONIC® Model 5433A/V or the Model 5832/S reusable safety cables are employed to make the connection between the temporary pacemaker and the proximal connector ends of the heart wire or temporary pacing lead. Alternatively, the MEDTRONIC® Model 5455/S or the Model 5833/S disposable cable is employed to make the connection between the temporary pacemaker and the proximal connector ends of a temporary pacing lead.

A similar situation arises during a surgical implantation of a pacemaker or pacemaker-cardioverter-defibrillator including a permanent cardiac lead or lead system or the replacement connection of a implantable pulse generator of one of these types with a pre-existing permanent cardiac lead or lead system. During or after implantation of the implantable cardiac lead(s), an external pacing system analyzer, e.g., the MEDTRONIC® Model No. 5311B PSA, is attached to the proximal lead connector end assembly accessible through the incision to assess the performance of the system. Again, the Model 5311B connector terminals are not compatible with the lead connector end elements for safety reasons. It is necessary to use either a disposable or a reusable "surgical cable" adaptor to complete the connection. Examples include the MEDTRONIC® Model 5410/S reusable surgical cable and the combination of the MEDTRONIC® Model 5411/S reusable adaptor and Model 5455/S disposable surgical cable.

Some of the above-identified patient and surgical cable adaptors constitute simply a connector assembly at one end that is compatible with the PSA or temporary pacemaker terminals, an external lead body enclosing the external lead conductors, and lead connector element connectors at the other end. Typically, two to four conductors are included in the lead body, and a set of two or four un-insulated alligator clips are provided at the other ends for attachment to the lead connector ring and pin of one or two implantable cardiac leads.

Other, typically reusable patient and surgical cables employ a mechanism for receiving the proximal connector ends of the heart wire, temporary pacing lead or permanent cardiac lead. For example, either RCA type female sockets are used or a dual thumb screw attachment mechanism is used in the above-referenced MEDTRONIC® Model 5832/S and Model 5433A/V reusable patient cables, respectively.

Commonly assigned U.S. Pat. Nos. 4,245,642 and 4,466,441 disclose medical lead adaptors of the latter type wherein lead connector end assemblies are insertable into sockets of a housing to make electrical contact with a single or two electrical contacts spaced apart therein to receive bifurcated bipolar, in-line bipolar, or unipolar lead connector rings and/or pins. The attachment is effected by tightening down thumb screws to prevent the connector end assemblies from slipping out of the socket openings of the housing in each case. It is not possible to make an attachment with a permanent pacing lead having a stylet wire fitted within the lead lumen and projecting out proximally through the connector pin . This case can only be accommodated by the use of alligator clips that attach across the connector rings and pins.

Such an attachment is not as secure and electrically isolated as would be desirable. It is undesirable to either lose the connection or to allow an electrical static discharge or other shock or impulse to reach the heart through the exposed lead connector ends. At present, it is necessary to loop and tape the assembled adaptor lead and implantable lead body against the patient's body and also place tape over the alligator clips.

At times, it has been observed that the careless use of alligator clips can damage the insulation sheathes adjacent to the lead connector end ring or connector pins. In IS-1 leads, damage to the insulating sheath and the seal rings on either side of the connector ring has been observed due to movement of the jaws of the alligator clips.

SUMMARY OF THE INVENTION

It is an object of the present invention to solve these problems identified with prior art methods and mechanisms for attaching an external medical device to an implantable cardiac lead of the types including permanent cardiac leads, temporary pacing leads and heart wires of the types having unipolar lead connector end assemblies or bipolar, in-line, lead connector end assemblies.

The medical lead adaptor of the present invention advantageously allows a wide range of connections to be made between diverse types of implantable medical leads and external medical devices. The medical lead adaptor of the present invention advantageously minimizes the risk of inadvertent release of contact with the lead conductor pin and ring. The medical lead adaptor of the present invention also is easily opened and closed with a simple push-button motion without the need to tighten down threaded thumb screws or the like. The medical lead adaptor minimizes the possibility of damage to the insulating sleeves of bipolar in-line cardiac lead connector assemblies.

Where the connection is with a permanently implantable, endocardial cardiac lead, the medical lead adaptor is configured to allow the stiffening stylet wire to remain within the lead lumen and extend proximally of the proximal connector pin. The stiffening stylet wire can therefore be manipulated, if necessary, to re-position the distal end of the lead while the external medical device remains attached to an external medical device through the connection with the medical lead adaptor. The secure attachment of the lead connector end assembly avoids inadvertent release during manipulation of the cardiac lead body and stiffening stylet wire. Moreover, the lead connector element(s), i.e., the lead connector ring and/or pin, are electrically isolated within a connector receptacle to avoid contact while manipulating the stiffening stylet wire and cardiac lead body.

In the particular configuration of the preferred embodiment, a variety of implantable lead connector end assemblies may be advantageously coupled to the medical lead adaptor including temporary pacing leads and heart wires that do not employ a stiffening stylet wire. In certain instances, the lead connector end assemblies of a permanent unipolar endocardial pacing lead and a temporary indifferent electrode bearing lead may be coupled to an external medical device through the medical lead adaptor.

The present invention is implemented in a preferred embodiment of a medical lead adaptor that provides a rapid, secure, insulated connection of the lead connector end assembly of one or more implantable cardiac lead of the types described above with an external medical device of one of the types described above. An adaptor connector assembly is coupled to one end of an external lead body having preferably two external electrical conductors therein each extending between a first external lead conductor end to a second external lead conductor end at the opposite ends of the external lead body. Each first external lead conductor end is electrically connected with an electrical receptacle contact aligned with a connector receptacle within the adaptor connector assembly. Each second external lead conductor end is coupled with an external lead connector element of an external lead connector assembly for making electrical contact with the connector terminal of the external medical device. It is contemplated that a variety of such medical lead adaptors with differing external lead connector end assemblies adapted to fit the connector terminals of differing external medical devices may be necessary.

In the preferred embodiment of the present invention, the adaptor connector assembly is configured with an elongated bipolar receptacle to accept a bipolar, inline, lead connector end assembly. The elongated bipolar receptacle includes proximal and distal receptacle contacts spaced apart from one another for making electrical contact with the proximal and distal connector elements of the bipolar, inline, lead connector end assembly. The proximal and distal receptacle contacts are each electrically connected with one of the first external lead conductor ends.

The elongated bipolar receptacle may also receive a unipolar lead connector end assembly having a configuration conforming with that of the bipolar lead connector end assembly and make electrical connection between the unipolar lead connector pin and the proximal receptacle contact.

The elongated bipolar receptacle is configured to receive a permanent, bipolar in-line or unipolar, lead connector end assembly with a stiffening stylet wire extending proximally thereof. In addition, such unipolar and bipolar permanent cardiac lead connector end assemblies may be received in the elongated bipolar receptacle without a stiffening stylet. It is also contemplated that the elongated bipolar receptacle may receive the lead connector end assemblies of other unipolar and bipolar permanent implantable cardiac leads not employing a stiffening stylet wire. In addition, it is contemplated that temporary pacing leads and heart wires that share compatible lead connector end assembly dimensions may be received in the elongated bipolar receptacle.

In addition, a separate pair of positive and negative polarity unipolar receptacles are provided for receiving connector pins of connector end assemblies of unipolar implantable or external medical leads. Each unipolar receptacle is aligned with a unipolar receptacle contact for making electrical and mechanical contact with a unipolar lead connector pin inserted therein. Preferably, each of the unipolar receptacle contacts are electrically connected to one of the first external lead conductor ends.

The receptacle contacts are movable together with movement of a spring loaded push-button mechanism from a normally closed or locked position to an open or unlocked position. In the normally closed position, the receptacle contacts block insertion of a lead connector end assembly into any of the unipolar receptacles and the elongated bipolar receptacle. On depression of the push-button, the receptacle contacts move to an open position for receiving or removing the lead connector end assemblies in or from the unipolar receptacles and the elongated bipolar receptacle. On release of the push-button, the receptacle contacts lock onto the lead connector end connector element(s) to resist removal of a lead connector end assembly from any of the unipolar receptacles and elongated bipolar receptacle.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like reference numbers designate like parts throughout the figures thereof, and wherein.

DETAILED DESCRIPTION OF THE PREFERRED EMBODIMENT

The preferred embodiment of the medical lead adaptor 10 for making a rapid electrical connection between external medical device connector terminals (not shown) and a proximal lead connector end assembly 12 of an implantable cardiac lead 14 is shown in the figures. The external medical device connector terminals may take any of the forms used with the above-referenced MEDTRONIC® Model 5311B PSA or Model 5348 and 5388 temporary pacemakers. The permanent implantable cardiac lead 14 is shown in part and includes an elongated implantable lead body 16 extending from the lead connector end assembly 12 toward the distal cardiac lead end (not shown). The distal cardiac lead end includes at least one electrode that is implanted in contact with a heart chamber of the patient 20, and may take any of the known forms for implantable cardiac leads of the type described above. The implantable lead body 16 contains an implantable lead conductor coupled between a distal electrode and a proximal lead connector element of the lead connector end assembly 12.

Figure 2:
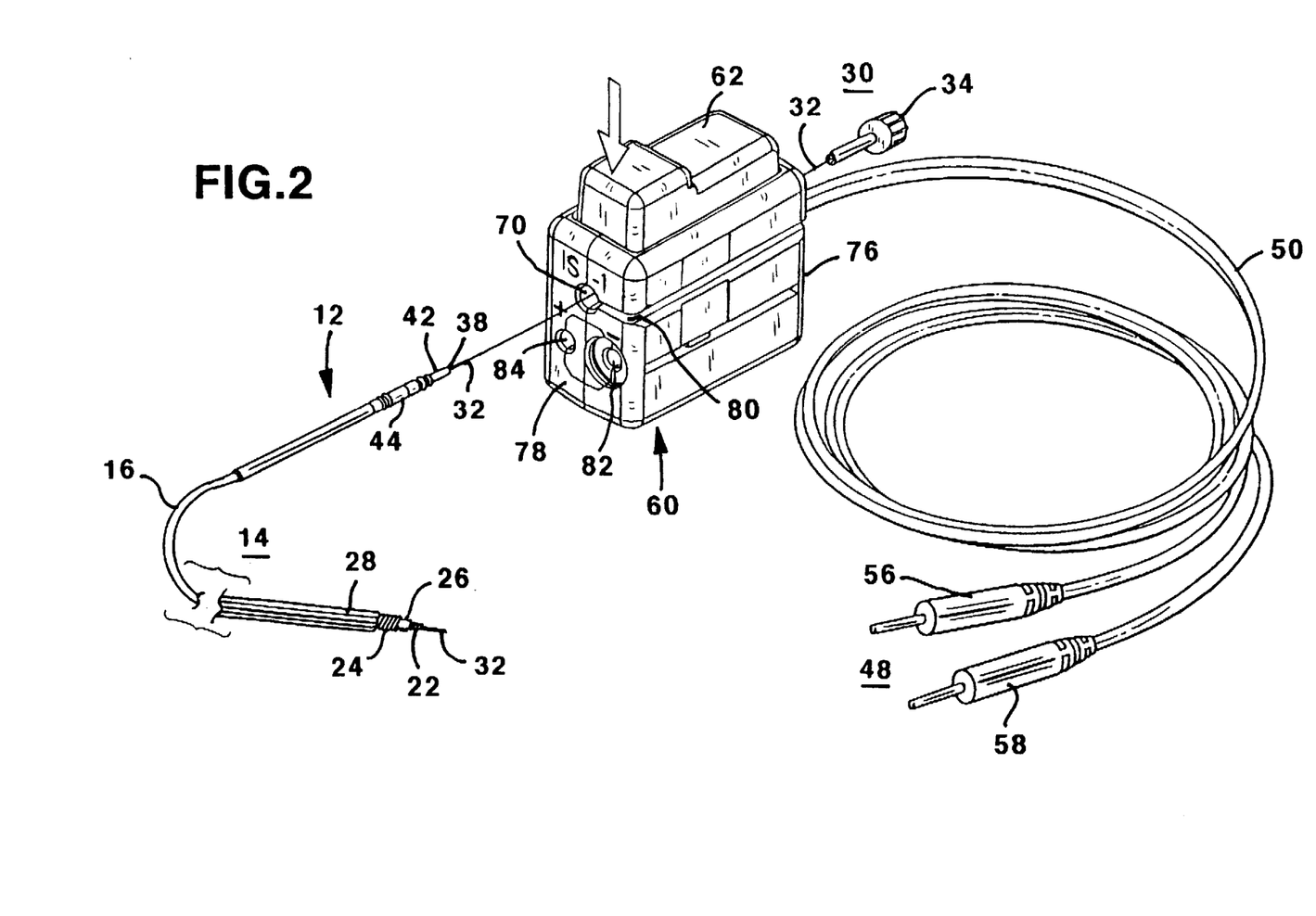
FIG. 2 is an isometric view of the proximal connector end assembly of a permanent bipolar cardiac lead inserted into a bipolar in-line connector receptacle of the medical lead adaptor of FIG. 1.
Figure 3:
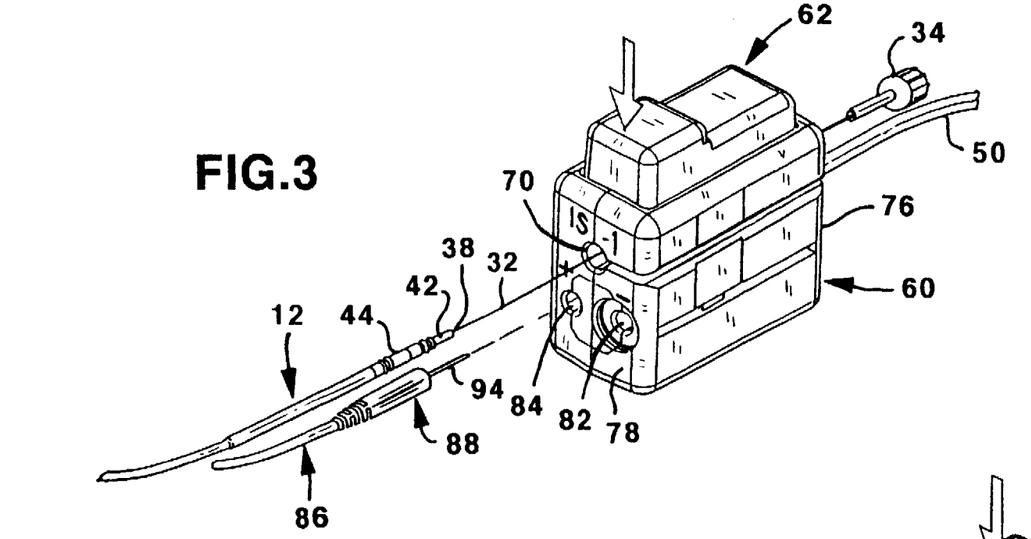
FIG. 3 is an isometric view of the proximal connector end assemblies of permanent bipolar and unipolar cardiac leads positioned to be inserted into a bipolar in-line connector receptacle and a further unipolar connector receptacle, respectively, of the medical lead adaptor of FIG. 1.

The implantable cardiac lead 14 is depicted in FIGS. 2 and 3 as a bipolar, inline, permanent cardiac pacing lead employing co-axially wound, coiled wire, implantable lead conductors 22 and 24 separated apart by an insulating sheath 26 and included within an outer insulating sheath 28. The outer implantable lead conductor 24 is coupled to a respective distal lead connector ring 44 and the inner implantable lead conductor 22 is coupled to a respective lead connector pin 42. These connections may be effected in the manner shown, for example, in the above-incorporated U.S. Pat. No. 5,007,435. A lumen is formed within the inner implantable lead conductor 24 for receiving a stiffening stylet wire 32 through a lumen end opening 38 in the lead connector pin 42. When the stylet wire 32 is received in the lumen, it extends proximally from the lumen end opening 38 so that the stylet knob 34 may be manipulated to rotate or axially extend or withdraw the stylet wire 32 with respect to the lead body lumen The medical lead adaptor 10 includes an external lead body 50 extending between first and second external lead conductor ends thereof. An external lead connector end assembly 48 of any of the types described above for making electrical contact with the external medical device connector terminals is coupled to the second external lead conductor end. Preferably, the external lead body 50 encases two electrically isolated external electrical conductors 52 and 54 (shown exposed in FIG. 5) of any known configuration which are coupled at their ends with two external lead connector pins 56 and 58 shown in FIG. 2.

An adaptor connector assembly 40 for receiving the lead connector end assembly 12 is formed at the first end of the external lead body 50 and includes a housing 60 and a push-button 62 that is depressed in the direction of the arrow shown in FIG. 2. The housing 60 is generally longitudinal having generally planar outer surface side walls and top and bottom walls extending between proximal and distal housing end walls 76, 78 thereof. The housing 60 includes the elongated bipolar receptacle 70 (best shown in FIG. 3) that extends from the proximal and distal housing end walls 76 and 78. The elongated bipolar receptacle 70 is shaped internally in diameter to conformably receive the lead connector end assembly 12 when it is inserted into the receptacle opening in distal housing end 78. In the preferred embodiment, it is dimensioned to receive either a unipolar or a bipolar, inline, lead connector end assembly 12 meeting the IS-1 standard, and for convenience is referred to as the IS-1 receptacle 70. As described below in reference to FIG. 5, it is necessary to depress the push-button 62 in the direction of the arrow in order to unblock the IS-1 receptacle 70 while axially inserting the proximal lead connector end assembly 12 toward the proximal end wall 76.

Figure 1:
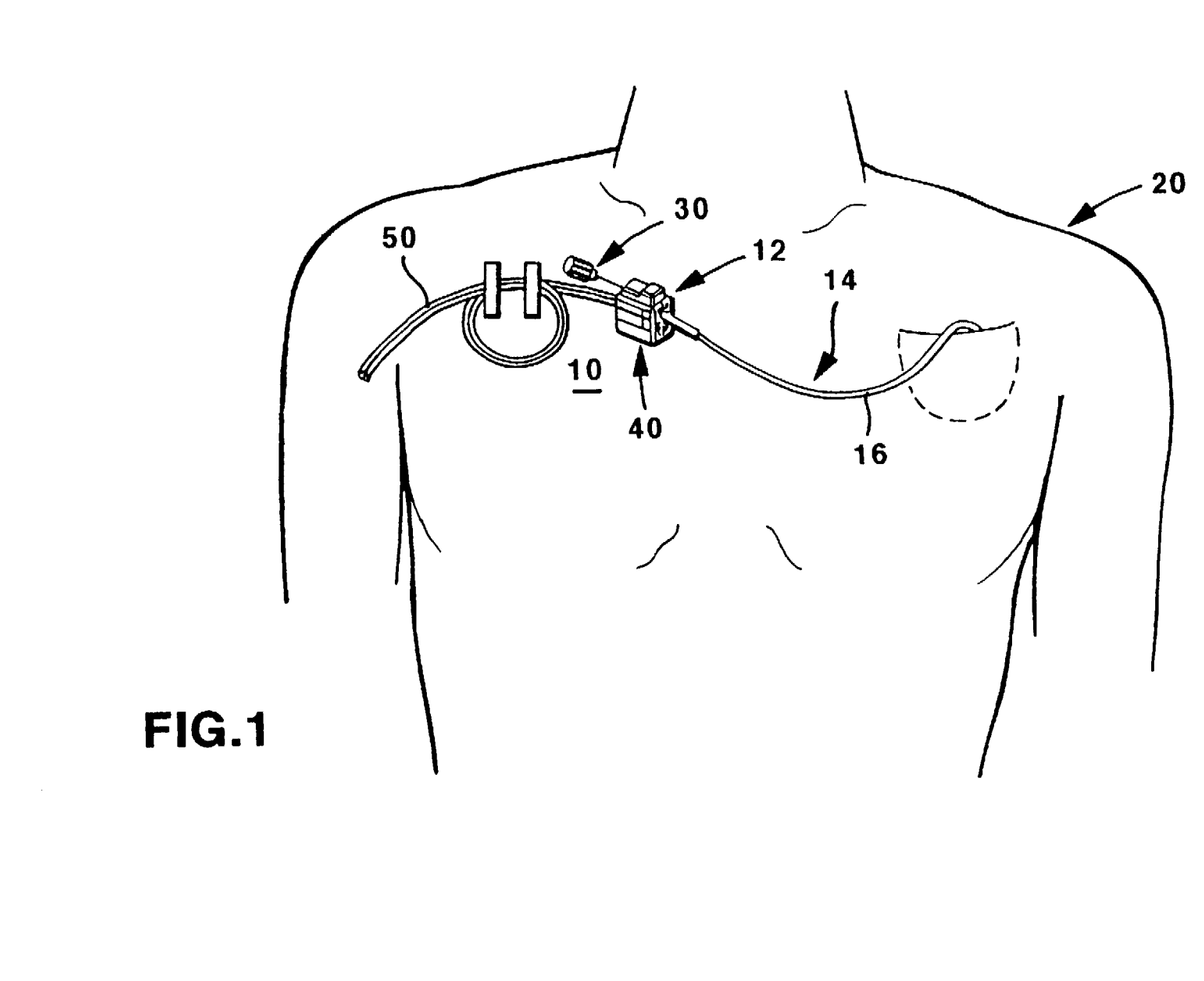
FIG. 1 is a simplified schematic view of an implanted permanent cardiac lead of the types described above implanted in a patient and coupled to the medical adaptor of the first preferred embodiment of the present invention.

If the implantable cardiac lead 14 includes a stylet wire 30 as depicted in FIGS. 1 and 2, it is first necessary to insert the stylet wire 32 into the IS-1 receptacle 70 and to then axially advance the implantable lead connector end assembly 12 proximally into the IS-1 receptacle 70. A housing slot 80 extends laterally of the IS-1 receptacle 70 to the exterior housing surface of the right side wall through which the stylet wire 32 may be laterally placed into the IS-1 receptacle 70 as depicted in FIG. 2. The housing slot 80 extends through the proximal and distal end walls 76 and 78, and a reduced size receptacle opening of the IS-1 receptacle 70 extends through the proximal end wall 76 so that the stylet wire 32 and knob 34 extend distally therefrom as shown in FIG. 2. The push-button 62 must be held depressed to unblock the IS-1 receptacle 70 in order to first laterally insert the stylet wire 32 through slot 80 and to then axially insert the lead connector end assembly 12 into the distal opening of the IS-1 receptacle 70. It is assumed that the push-button is forced down in FIG. 2 and the stylet wire 32 has been inserted laterally through the housing slot 80 into the open IS-1 receptacle 70. The lead connector end assembly 12 is poised to be advanced into the IS-1 receptacle 70.

As stated above, the IS-1 receptacle 70 is preferably configured dimensionally internally to receive an in-line bipolar permanent cardiac lead connector end assembly 12 that complies with the IS-1 dimensional standard, and the distal end wall 78 is labeled "IS-1" near its distal wall receptacle opening. At least the lead connector ring and pin 44 and 42 of the lead connector end assembly 12 are received in the elongated receptacle 70 between the proximal and distal housing end walls 76, 78 so that they are not exposed when locked therein.

The IS-1 receptacle 70 can therefore receive either a bipolar IS-1 lead connector end assembly 12 as depicted in FIG. 2 or a unipolar IS-1 lead connector end assembly of the same dimensions but only having the connector pin 42. In either case, the stylet 30 may be used or not used. Moreover, the stylet wire 32 may be inserted or withdrawn from the implantable lead lumen opening 38 while the lead connector end assembly 12 is received and locked into the IS-1 receptacle 70.

Figure 4:
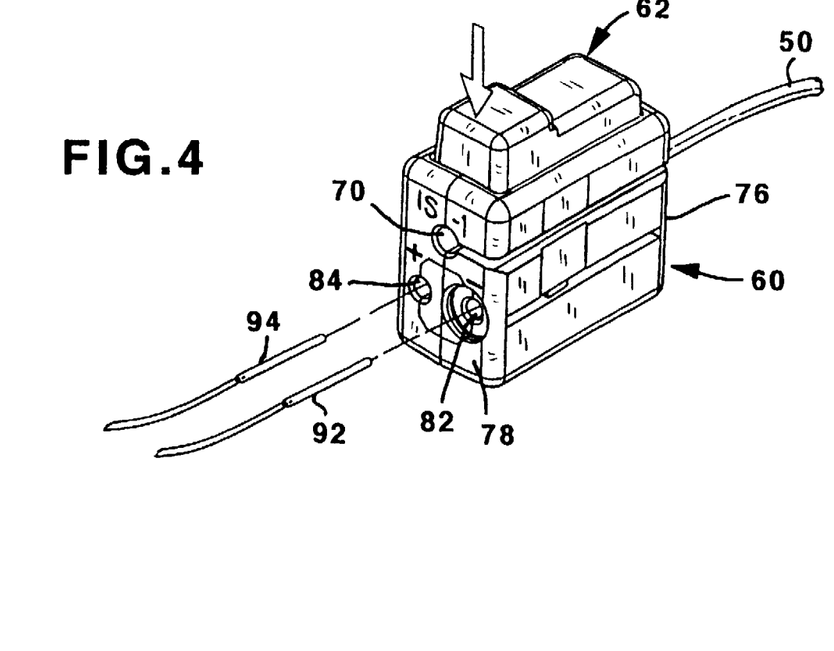
FIG. 4 is an isometric view showing the proximal connector pins of unipolar or bifurcated bipolar temporary pacing leads or heart wires and/or an indifferent electrode bearing lead positioned to be inserted into the unipolar connector receptacles of the medical lead adaptor of FIG. 1.

Two unipolar "negative" and "positive" unipolar receptacles 82 and 84 are formed within the housing 60 for receiving unipolar connector pins of temporary pacing leads or heart wires or at least one indifferent electrode bearing lead as shown in FIGS. 3 and 4. The unipolar receptacles 82 and 84 do not extend to the proximal end wall 76. The distal end wall 78 is labeled "−" and "+" adjacent to the distal wall openings to the negative and positive unipolar receptacles 82 and 84, respectively. Typical unipolar connector pins 92 and 94 of temporary pacing leads or heart wires of the types described above are depicted in FIG. 4 ready to be inserted axially into the unipolar receptacles 82 and 84 when the push-button 62 is depressed in the unlock direction of the arrow. In such a use, both of the electrodes of the temporary leads or heart wires attached to the unipolar lead connector pins 92, 94 can be attached to the patient's heart for temporary pacing. All of the above-referenced MEDTRONIC heart wire and temporary pacing lead models other than the TEMPTRON temporary lead employ bifurcated lead connector end assemblies terminating in separated connector pins 92 and 94. However, an indifferent electrode on the patient's skin and connected to a connector pin of the same type can be substituted for one of the implanted bipolar heart wire or temporary pacing lead connector pins 92 or 94, depending on maintaining the proper polarity. As described below, the negative and positive unipolar receptacles 82 and 84 are sized in conjunction with the contacts therein to accept the range of diameters of lead connector pins 92 and 94 in current use.

As shown below, the positive receptacle contact of the positive unipolar receptacle 84 is electrically coupled internally with the ring receptacle contact of the IS-1 receptacle 70. Similarly, the negative receptacle contact of the negative unipolar receptacle 82 is electrically coupled internally with the pin receptacle contact of the IS-1 receptacle 70. Depending on the relative sizes, it may be possible to electrically interconnect the connector ring and pin 44 and 42 of a bipolar in-line lead connector end assembly 12 inserted into the IS-1 receptacle 70 with respective unipolar connector pins 94 and 92 inserted into the unipolar receptacles 84 and 82.

Figure 9:
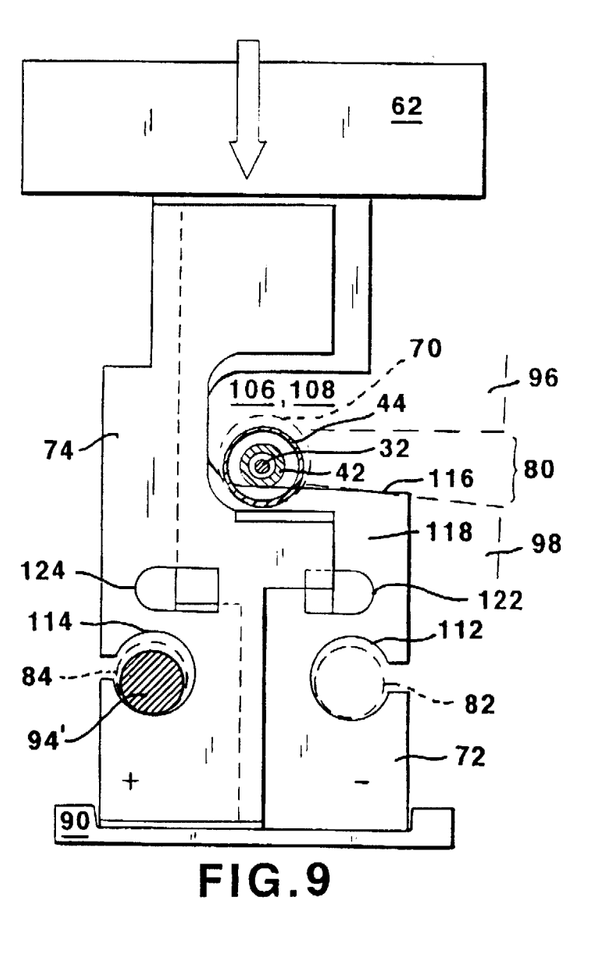
FIG. 9 is a plan view illustrating the alignment of the contact blades and the positive and negative unipolar receptacles as well as the elongated receptacle of the adaptor connector assembly of FIG. 5 in the open position allowing insertion of a positive unipolar lead connector pin in the positive unipolar receptacle and into contact with the unipolar receptacle contact therein and allowing insertion of the bipolar lead connector end assembly into the elongated receptacle so that the bipolar lead connector pin is in contact the elongated receptacle pin contacts of a contact blade with the stylet in the lead lumen.

FIG. 3 depicts a situation that may arise where the physician prefers to employ a separate large surface area indifferent electrode contacting the patient's skin, for example, instead of the bipolar lead ring electrode (not shown) coupled to the connector ring 44 of the implantable cardiac lead 14. The physician may wish to test the efficacy of unipolar sensing or pacing in a patient on a temporary basis. Or, the external monitoring equipment available may be more sensitive to the far field unipolar ECG signal than the near field bipolar EGM signal derived between the distal tip and ring electrodes in contact with the patient's heart. In this illustration, therefore, the connector pin 94' of a further temporary external lead 86 (or a further external cable coupled to such a lead) coupled at its distal end directly or indirectly to the indifferent electrode (not shown) is inserted into the positive unipolar receptacle 84. The pin diameter of the connector pin 94' is sized to effectively deflect the receptacle contact in such a way as to move the ring receptacle contact coupled with it out of contact with the connector ring 44 within the IS-1 receptacle 70. This particular relationship is illustrated in FIG. 9 and described further below. Alternatively, a unipolar lead having a unipolar lead connector end assembly satisfying the IS-1 standard could be substituted for the bipolar, in-line cardiac lead 14 in the illustration of FIG. 3 for use with the indifferent electrode bearing lead 86.

Figure 5:
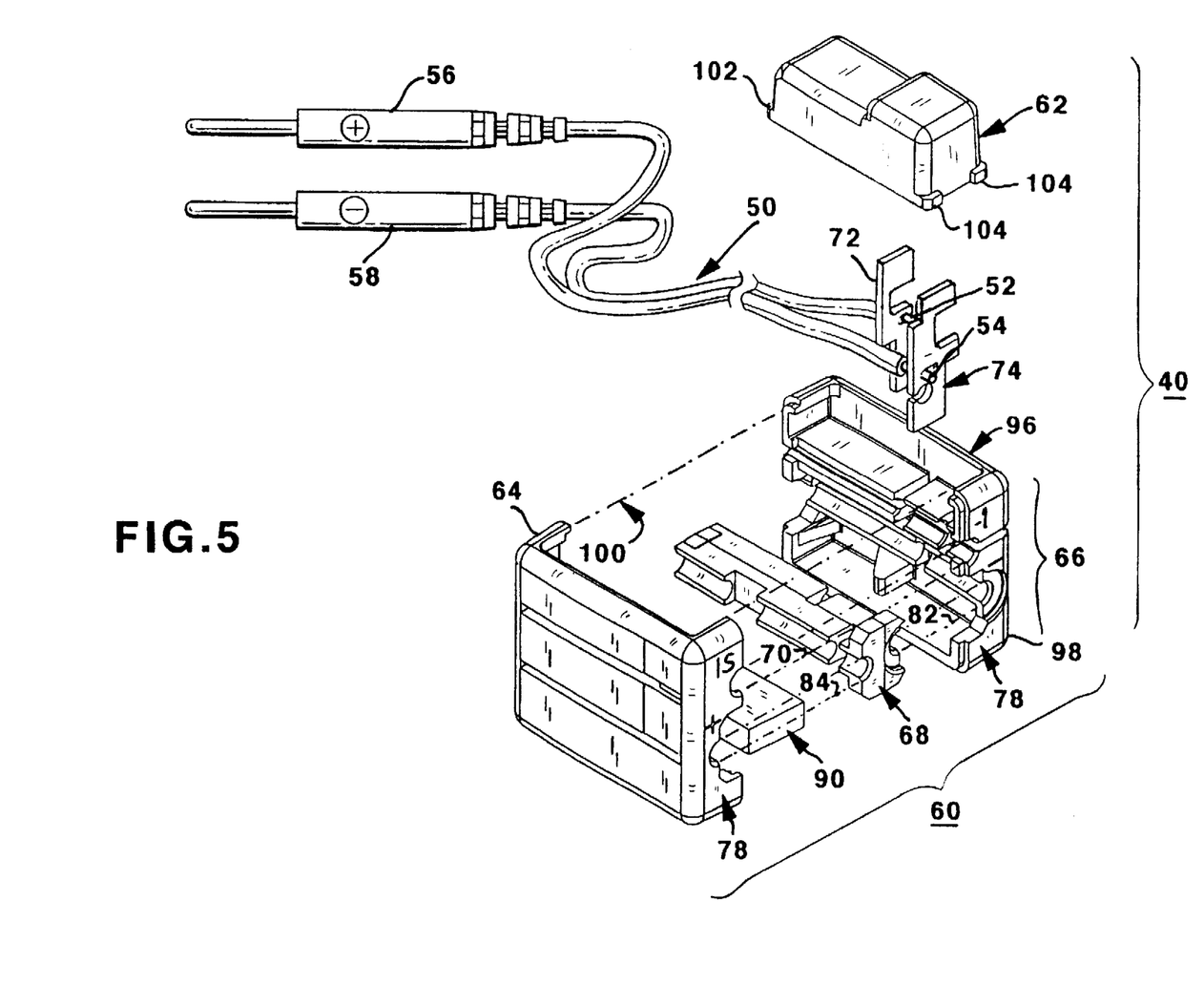
FIG. 5 is an exploded isometric view of the interior components of the medical lead adaptor of FIG. 1.
Figure 6:
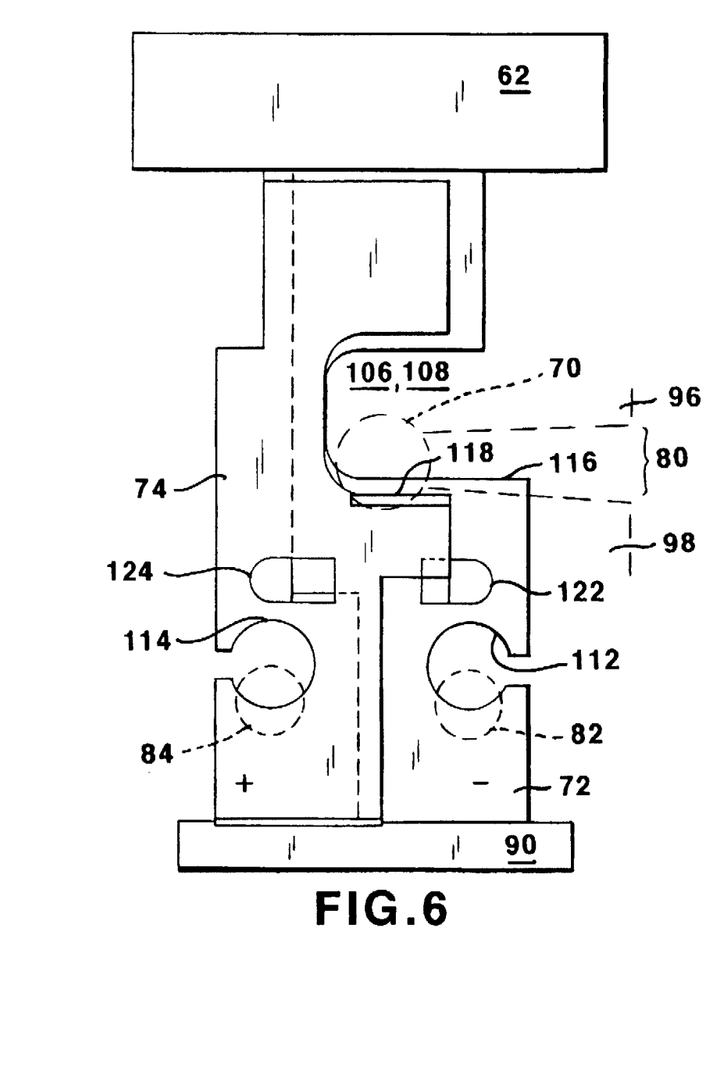
FIG. 6 is a plan view illustrating the alignment of the contact blades and elongated receptacles of the adaptor connector assembly of FIG. 5 in the closed position blocking insertion of a lead connector end assembly.
Figure 7:
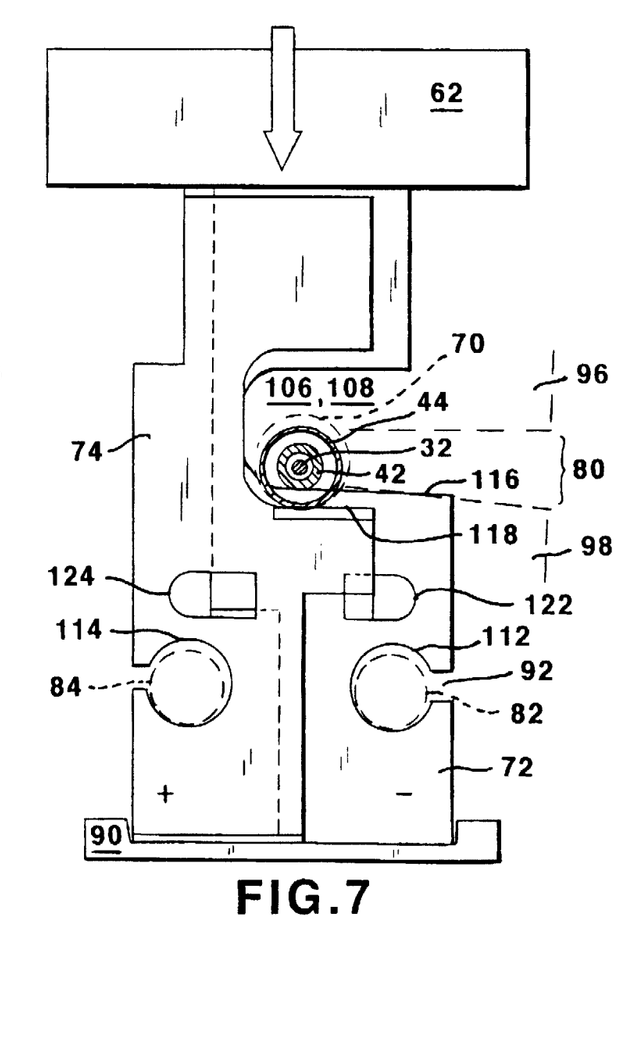
FIG. 7 is a plan view illustrating the alignment of the contact blades and elongated receptacle of the adaptor connector assembly of FIG. 5 in the open position allowing insertion of a bipolar lead connector end assembly therein and into contact with the elongated receptacle contacts of the contact blades with the stylet in the lead lumen.

The interior configuration of the IS-1 receptacle 70 and the unipolar receptacles 82 and 84 and the receptacle contacts that make electrical contact with and mechanically retain the lead connector elements therein are shown in FIGS. 5–7. The exploded view of FIG. 5 depicts the assembly relation of the components of the housing 60 which include a housing left half 64, a housing right half 66 and an interior insert 68, an interior spring block 90 and proximal and distal contact blades 72 and 74. The proximal and distal contact blades 72 and 74 are attached to the ends of the external lead conductors 52 and 54, respectively, of the external lead body 50 which exits through an opening in the proximal end wall 76. In the assembly depicted in FIG. 5, the distal ends of the external lead conductors 52 and 54 are inserted into the openings 122 and 124 (shown in FIGS. 6 and 7) in the proximal and distal contact blades 72 and 74 and are attached thereto.

The housing right half 66 is separated into an upper right half 96 and a lower right half 98 by the elongated lateral slot 80. Each of the housing left half 64, housing right half 66 and interior insert 68 are formed with mating edges. The mating edges allow them to be snapped and adhered together to form the housing 60 and with a set of interior spaces and slots depicted in FIG. 5 enclosing the spring block 90 and the proximal and distal contact blades 72 and 74.

A top surface opening 100 is defined when the housing components are assembled that receives and captures the proximal and distal edge tabs 102, 104 of the spring-loaded push-button 62. The push-button 62 is attached in its interior surface to the upper ends of the proximal and distal contact blades 72 and 74. A spring block 90, formed of a non-conductive, resilient, plastic material in a block form as shown or in a leaf spring form, is captured in a lower chamber formed when the housing components are assembled together. The spring block 90 bears against the lower edges of the proximal and distal contact blades 72 and 74. The proximal and distal contact blades 72 and 74 extend through proximal and distal blade slots formed in the housing left and right halves 64, 66 and interior insert 68 so that they are guided and electrically separated and can be simultaneously pressed down. The spring block 90 biases the contact blades upward so that the proximal and distal push-button edge tabs 102, 104 firmly engage the interior rim of the upper opening 100. In this condition, the proximal and distal contact blades 72 and 74 transversely intersect the IS-1 receptacle 70 and the unipolar receptacles 82 and 84 and block the axial insertion of any of the compatible lead connector end assemblies into them as shown in FIG. 6. The lateral insertion of the stylet wire 32 through the lateral slot 80 and into the IS-1 receptacle 70 is also blocked by the proximal and distal contact blades 72 and 74 as shown in FIG. 6. In effect, the elongated receptacle contacts block the IS-1 receptacle 70 and laterally extending slot 80, and the unipolar receptacle contacts block the positive and negative unipolar receptacles 84 and 82.

The inward depression of the push-button 62 in the direction of the arrow forces the proximal and distal contact blades 72 and 74 downward together, compressing the spring block 90 and moving the proximal and distal contact blades 72 and 74 into an open or unlocked position. In the open or unlocked position, a first set of axially aligned, U-shaped openings 106 and 108 in the proximal and distal contact blades 72 and 74 are aligned, at least at their lower contact edges 116 and 118, with the respective IS-1 receptacle 70 and the laterally extending longitudinal slot 80. In addition, in the open position, at least a lower edge receptacle contact of a circular opening 112 in the proximal contact blade 72 is aligned with the negative unipolar receptacle 82. Similarly, in the open position, at least a lower edge receptacle contact of a circular opening 114 in the distal contact blade 74 is aligned with the positive unipolar receptacle 84. When either of the unipolar cardiac lead connector pins 92 and/or 94 are inserted across the circular openings 112 and 114, the receptacle contact holds the push-button 62 and proximal and distal contact blades 72 and 74 down. The resistance of the spring block 90 acting through the receptacle contacts retains the unipolar cardiac lead connector pins 92 and/or 94 in the negative and/or positive unipolar receptacles 82 and/or 84.

When the lead connector end assembly 12 is inserted into the IS-1 receptacle 70, and the push-button 62 is released, the connector pin 42 bears against the lower edge receptacle contact 116 of the U-shaped opening 106 formed in the proximal contact blade 72 in the locked position as shown in FIG. 7. Simultaneously, bipolar lead connector ring 44 bears against the lower edge receptacle contact 118 of the U-shaped opening 108 formed in the distal contact blade 74. The stylet wire 32 extends through the lumen of the cardiac lead 14 and out of the lumen end opening 38 and through a proximal end opening of the IS-1 receptacle 70 in the proximal end wall 76 (shown in FIG. 5). Again, the resistance of the spring block 90 forces the receptacle contacts 116 and 118 against the connector pin and ring 42 and 44 to hold the implantable cardiac lead end assembly 12 in place.

In use, the open position is maintained by inward depression of push-button 62 as the stylet wire 32 is inserted laterally through the laterally extending slot 80. The lead connector end assembly 12 is inserted axially into the elongated receptacle 70. The lead connector pin 42 and ring 44 are inserted through the aligned contact blade openings 106 and 108 and fully seated in the IS-1 receptacle 70. The in-line lead connector end assembly 12 is fully seated such that the distal connector ring 44 and the proximal connector pin 42 are aligned within the aligned opening edge receptacle contacts 118 and 116. After seating is visually and tactually confirmed, the push-button 62 is released from the open position. The spring block 90 forces the receptacle contacts of the opening edge receptacle contacts 116 and 118 against the lead connector pin 42 and ring 44, respectively, and provides firm electrical contact therebetween. The force locks the lead connector end assembly 12 from withdrawal back out of the IS-1 receptacle 70 opening in the distal end wall 78. The stylet wire 32 may be left in place, advanced or withdrawn from the lead lumen, or otherwise used to manipulate the distal end of the lead without disturbing the electrical and mechanical connection effected with the medical lead adaptor.

Figure 8:
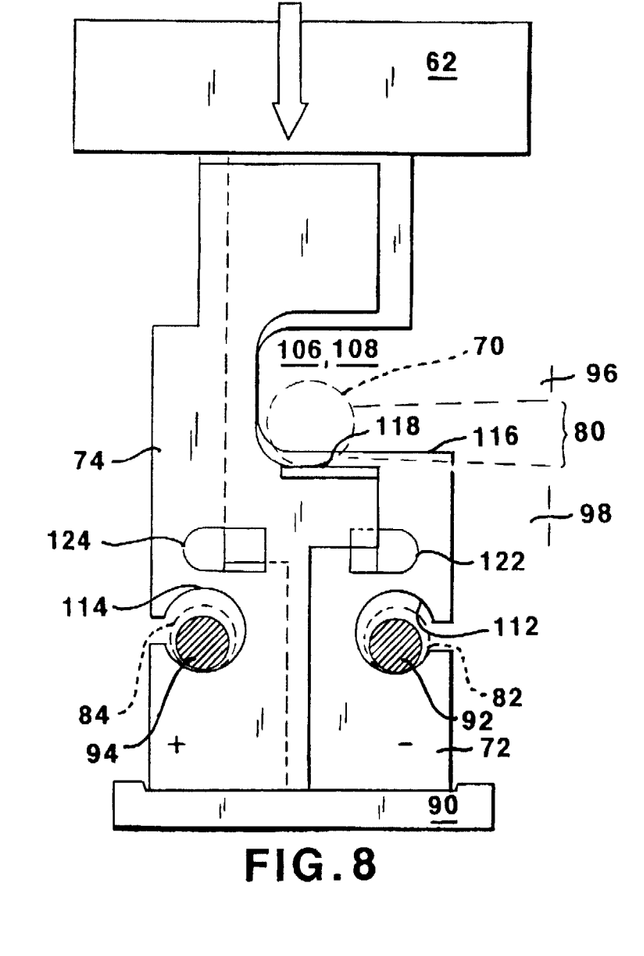
FIG. 8 is a plan view illustrating the alignment of the contact blades and the positive and negative unipolar receptacles of the adaptor connector assembly of FIG. 5 in the open position allowing insertion of unipolar lead connector pins therein and into contact with the unipolar receptacle contacts of the contact blades.

FIG. 8 is a plan view illustrating the alignment of the contact blades 74 and 72 and the positive and negative unipolar receptacles 84 and 82 of the adaptor connector assembly of FIG. 5 in the open position allowing insertion of unipolar lead connector pins 94 and 92 therein and the locked position locked them in place. When the pushbutton 62 is depressed, the generally circular unipolar openings 114 and 112 are moved from the locked position into alignment with the unipolar receptacles 84 and 82. The unipolar lead connector pins 94 and 92 can then be inserted through the aligned unipolar opening 114 and unipolar receptacle 84 and unipolar opening 112 and unipolar receptacle 82, respectively. The lower edges of the openings 112 and 114 function as the unipolar receptacle contacts for the unipolar lead connector pins 92 and 94 for the various types of unipolar leads described above. The negative and positive lead connector end assemblies 92 and 94 are retained in the negative and positive unipolar receptacles 82 and 84 by the spring force acting through the edges of openings 112 and 114 in the locked position.

It will also be understood that a permanently implantable unipolar lead connector pin may be inserted into the negative or positive unipolar receptacle 82 or 84 with an indifferent electrode bearing lead connector end connector pin inserted into the other unipolar receptacle. Moreover, in cases where bipolar or multi-polar implantable cardiac leads employ bifurcated proximal connector end assemblies terminating in unipolar-type connector pins, they can be inserted into the negative and positive unipolar receptacles 82 and 84. In addition, if the dimensions are consistent, the connector end assemblies of bipolar, in-line temporary pacing leads may be inserted into the IS-1 receptacle 70 for attachment to an external medical device. The principals of the present invention may be extended to permutations and combinations of such implantable cardiac leads.

To obtain the function described above with respect to FIG. 3, the lower edges of the circular opening 114 and the U-shaped opening 118 are dimensioned apart so that a relatively large diameter connector pin 94' of unipolar lead 86 virtually filling the unipolar receptacle 84 will draw the contact blade 74 downward. When this occurs, the receptacle contact 118 of U-shaped opening 108 is drawn away from the elongated IS-1 receptacle 70. Therefore, when a bipolar IS-1 compatible lead connector end assembly is inserted into the IS-1 receptacle, electrical contact is prevented between the connector ring 44 and the lower edge contact 118. In this manner, a remote indifferent electrode coupled to the unipolar lead 86 can be substituted for the indifferent ring electrode of the bipolar in-line implantable cardiac lead 14. FIG. 9 is a plan view illustrating this alignment of the contact blades 72 and 74 with respect to the positive unipolar receptacle 84 and the elongated receptacle 70 in a such a locked position. In this illustrated position, it may be seen that the receptacle contact 118 is spaced apart from the connector ring 44, while the connector pin 42 is in contact with the edge opening receptacle contact 116.

It will also be apparent that a unipolar IS-1 lead connector end assembly not having a connector ring 44 may be inserted into the IS-1 receptacle, and the unipolar connector pin 94' of an indifferent electrode bearing unipolar lead 86 may be inserted into the positive unipolar receptacle 84 to make the connection illustrated in FIG. 9.

The preferred embodiment is described above in the context of a bipolar permanent cardiac lead having an in-line connector end assembly 12 conforming with the IS-1 standard. It will be understood that the above-described components of the adaptor connector assembly 40 may be modified to accept other bipolar, inline leads.

The external connector assembly 40 of the present invention can also be modified by suitably shaping and sizing the elongated receptacle 70 and adding a further spaced apart receptacle blade contacts to accept in-line, tri-polar, implantable medical leads. A further, parallel oriented, distal contact blade coupled to a further external lead conductor can be employed to make a separate electrical connection with the further connector ring of the tri-polar lead connector end assembly.

The preceding specific embodiment is illustrative of the practice of the invention in a preferred embodiment. It is understood therefore that other expedients and equivalents of disclosed components or functions known to those of skill in the art or otherwise disclosed herein may be employed in practicing the invention without departing from the invention or the scope of the following claims. In this regard, the particular shape of the lead connector end assemblies and the lead connector elements incorporated therein may take any form or arrangement that may be matched in a complementary fashion by the components forming the elongated bipolar receptacles and the bipolar receptacle. Similarly, the form, number and spacing apart of the contact blades and the openings formed therein for making contact with the lead connector elements may be modified to be compatible therewith and serve the purposes described above.

Moreover, the present invention may be employed in medical lead adaptors for making connections between other implantable or external medical leads and external medical equipment. For example, a medical lead adaptor may be configured following the above-described principles of the present invention to make electrical connections between implantable nerve, muscle or brain stimulation electrode bearing leads and external stimulators or test equipment.

The medical lead adaptor of the present invention is intended to accomodate a wide range of implantable medical lead connector end assemblies that fit within the elongated bipolar receptacle and the unipolar receptacles. However, because the lead connector end assemblies of permanent pacing leads, particularly, older lead models already implanted in patients, are not consistent in dimensions, e.g. the spacing between and diameters of the connector ring and pin of bipolar, in-line pacing leads, it may be necessary to provide a variety of medical lead adaptors with compatibly dimensioned connector receptacles and spaced apart receptacle contacts. Similarly, it may be necessary to provide a variety of medical lead adaptors with compatibly dimensioned connector receptacles and receptacle contacts to accommodate the lead connector ring and/or pin of heart wires and temporary pacing leads that differ dimensionally from one another and those of permanent cardiac leads.

The present invention further includes within its scope methods of using the medical lead adaptors of the present invention.

In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

We claim:

1. An external medical lead adaptor for making a rapid electrical connection between an external medical device connector terminal and a proximal lead connector end assembly of an implantable cardiac lead of the type having an elongated implantable lead body extending from the lead connector end assembly toward the distal cardiac lead end, the implantable lead body containing an implantable lead conductor coupled to a proximal lead connector element of the lead connector end assembly and having a lumen formed therein for receiving a stylet wire through a lumen end opening, whereby the stylet wire, when received in the lumen, extends proximally from the lumen end opening of the lead connector end assembly so that the stylet wire may be manipulated, the medical lead adaptor comprising:

external conductor means having at least one external electrical conductor therein extending between a first external conductor end thereof to a second external conductor end formed with an external connector element for making electrical contact with the external medical device connector terminal; and an adaptor connector assembly for receiving the lead connector end assembly and for making electrical contact between each respective implantable lead connector element and each external electrical conductor, the adaptor connector assembly having a proximal end wall and a distal end wall and side walls therebetween defining an adapter connector housing and further comprising:

receiver means internal to the adaptor connector assembly defining an elongated receptacle extending from a proximal end opening to a distal end opening shaped to conformably receive each lead connector element of the lead connector end assembly when inserted axially therein;

elongated receptacle contact means positioned along said elongated receptacle for making electrical contact with a lead connector element when inserted axially into the elongated receptacle;

means for electrically connecting said elongated receptacle contact means with said first external conductor end;

slot means extending laterally of said elongated receptacle through a side wall of said adaptor connector assembly to an exterior surface thereof for laterally receiving the stylet wire extending proximally from said lumen end opening of said lead connector end assembly to position the stylet wire to extend proximally from said proximal end wall when said lead connector end assembly is axially inserted into said elongated receptacle; and locking means coupled with said elongated receptacle contact means and manipulatable from a normally closed position, blocking lateral insertion of said stylet wire through said slot means into said elongated receptacle and extending through said distal end wall and blocking axial insertion of said lead connector end assembly into said elongated receptacle, to an open position with respect to said slot means and said elongated receptacle, for allowing said stylet wire extending proximally from said lumen end opening to be inserted laterally through the slot means into the elongated receptacle and for then allowing the implantable lead connector end assembly to be axially inserted into a distal end opening of said elongated receptacle, and to a locked position, wherein said elongated receptacle contact means is applied against a lead connector element with force resisting withdrawal of said lead connector end assembly from said elongated receptacle and assuring secure electrical contact between said elongated receptacle contact means and said lead connector element while allowing manipulation of the stylet wire with respect to said lumen.

2. The external medical lead adaptor of claim 1 wherein said elongated receptacle contact means is movable with respect to said elongated receptacle and said locking means is operable to dispose said elongated receptacle contact means into an interference relationship with said elongated receptacle and said slot means in said normally closed position.

3. The external medical lead adaptor of claim 2, wherein said locking means further comprises spring means internal to said adaptor connector assembly coupled with said elongated receptacle contact means for biasing said elongated receptacle contact means into said interference relationship and a push-button extending through a wall of said adaptor connector assembly and coupled to said elongated receptacle contact means that is manipulatable for moving said elongated receptacle contact means against said spring means and out of said interference relationship into said open position.

4. The external medical lead adaptor of claim 1, wherein:

said implantable cardiac lead comprises a bipolar cardiac lead having an elongated, in-line, lead connector end assembly formed with a proximal connector pin and a more distal connector ring;

said elongated receptacle is configured to receive said elongated bipolar, in-line lead connector end assembly;

said elongated receptacle contact means comprises a proximal connector pin receptacle contact and a more distal connector ring receptacle contact;

said external conductor means has first and second external electrical conductors therein each extending between a first external conductor end thereof to a second external conductor end thereof formed with an external connector element for making electrical contact with the external medical device connector terminal; and said electrically connecting means comprises first means for coupling said proximal connector pin receptacle contact with said first external conductor end of said first external electrical conductor and second means for coupling said connector ring receptacle contact with said first external conductor end of said second external electrical conductor.

5. The external medical lead adaptor of claim 4, wherein said elongated receptacle contact means is movable with respect to said elongated receptacle and said locking means is operable to dispose said proximal connector pin receptacle contact and distal connector ring receptacle contact into interference relationship with said elongated receptacle and said slot means in said normally closed position.

6. The external medical lead adaptor of claim 5, wherein said locking means further comprises:

spring means internal to said adaptor connector assembly coupled with said elongated receptacle contact means for biasing said proximal connector pin receptacle contact and said distal connector ring receptacle contact into said interference relationship with said elongated receptacle and said slot means in said normally closed position; and a push-button extending through a wall of said adaptor connector assembly and coupled to said proximal connector pin receptacle contact and distal connector ring receptacle contact that is manipulatable for moving said proximal connector pin receptacle contact and said distal connector ring receptacle contact against said spring means and out of said interference relationship into said open position.

7. The external medical lead adaptor of claim 6, wherein said receiver means further comprises first and second, spaced apart, unipolar receptacles for receiving unipolar lead connector pins of first and second unipolar implantable cardiac leads, and further comprising:

a first unipolar receptacle contact positioned along said first unipolar receptacle for making electrical contact with a first unipolar lead connector element when inserted axially into said first unipolar receptacle; and a second unipolar receptacle contact positioned along said second unipolar receptacle for making electrical contact with a second unipolar lead connector element when inserted axially into said second unipolar receptacle.

8. The external medical lead adaptor of claim 7, wherein said electrically connecting means comprises first means for coupling said first unipolar receptacle contact with said first external conductor end of said first external electrical conductor and second means for coupling said second unipolar receptacle contact with said first external conductor end of said second external electrical conductor.

9. The external medical lead adaptor of claim 4, wherein said receiver means further comprises first and second, spaced apart, unipolar receptacles for receiving unipolar lead connector pins of first and second unipolar implantable cardiac leads, and further comprising:

a first unipolar receptacle contact positioned along said first unipolar receptacle for making electrical contact with a first unipolar lead connector element when inserted axially into said first unipolar receptacle; and a second unipolar receptacle contact positioned along said second unipolar receptacle for making electrical contact with a second unipolar lead connector element when inserted axially into said second unipolar receptacle.

10. The external medical lead adaptor of claim 9, wherein said electrically connecting means comprises first means for coupling said first unipolar receptacle contact with said first external conductor end of said first external electrical conductor and second means for coupling said second unipolar receptacle contact with said first external conductor end of said second external electrical conductor.

11. The external medical lead adaptor of claim 10, wherein:

said contact means further comprises:

a first elongated contact blade formed with said proximal connector pin receptacle contact and said first unipolar receptacle contact at spaced apart locations therein and electrically connected to said first end of said first external conductor; and a second elongated contact blade formed with said distal connector ring receptacle contact and said second unipolar receptacle contact at spaced apart locations therein and electrically connected to said first end of said second external conductor, and said adaptor connector housing further comprises means for separating said first and second contact blades and for orienting said proximal connector pin receptacle contact and said distal connector ring receptacle contact at spaced apart locations along said elongated receptacle and for orienting said first unipolar receptacle contact with respect to said first unipolar receptacle and said second unipolar receptacle contact with respect to said second unipolar receptacle.

12. The external medical lead adaptor of claim 11, wherein said locking means further comprises:

spring means internal to said adaptor connector assembly coupled with a first end of said first and second elongated contact blades for biasing said proximal connector pin receptacle contact and said distal connector ring receptacle contact into said interference relationship with said elongated receptacle and said slot means in said normally closed position and for biasing said first and second unipolar receptacle contacts into an interference relationship with said first and second unipolar receptacles in said normally closed position; and a push-button extending through a wall of said adaptor connector assembly and coupled to second ends of said first and second elongated contact blades that may be depressed for moving said first and second elongated contact blades against said spring means and for thereby moving said proximal connector pin receptacle contact and said distal connector ring receptacle contact and said first and second unipolar receptacle contacts out of said interference relationship into said open position.

13. The external medical lead adaptor of claim 1, wherein:

said implantable cardiac lead comprises a cardiac lead having a lead connector end assembly formed with at least a proximal connector pin;

said elongated receptacle is configured to receive said elongated lead connector end assembly;

said elongated receptacle contact means comprises a proximal connector pin receptacle contact;

said external conductor means has first and second external electrical conductors therein each extending between a first external conductor end thereof to a second external conductor end thereof formed with an external connector element for making electrical contact with the external medical device connector terminal;

said receiver means further comprises a first unipolar receptacle for receiving a unipolar lead connector pin of a first unipolar implantable cardiac lead and a first unipolar receptacle contact positioned along said first unipolar receptacle for making electrical contact with a first unipolar lead connector pin when inserted axially into said first unipolar receptacle; and said electrically connecting means comprises first means for coupling said proximal connector pin receptacle contact with said first external conductor end of said first external electrical conductor and second means for coupling said first unipolar receptacle contact with said first external conductor end of said second external electrical conductor.

14. The external medical lead adaptor of claim 1, wherein:

said implantable cardiac lead comprises a bipolar cardiac lead having an inline lead connector end assembly formed with at least a proximal connector pin and a more distal connector ring;

said elongated receptacle is configured to receive said elongated in-line lead connector end assembly;

said elongated receptacle contact means comprises a proximal connector pin receptacle contact and a more distal connector ring receptacle contact; and said receiver means further comprises first and second unipolar receptacles for receiving a unipolar lead connector pin of a first and a second unipolar cardiac lead and a first and a second unipolar receptacle contact positioned along said first and second unipolar receptacle for making electrical contact with a first and a second respective unipolar lead connector pin when inserted axially into said first and second unipolar receptacle; and said electrically connecting means comprises first means for coupling said proximal connector pin receptacle contact and said first unipolar receptacle contact with said first external conductor end of said first external electrical conductor and second means for coupling said distal connector ring receptacle contact and said second unipolar receptacle contact with said first external conductor end of said second external electrical conductor.

15. The external medical lead adaptor of claim 14, wherein:

said contact means further comprises:

a first elongated contact blade formed with said proximal connector pin receptacle contact and said first unipolar receptacle contact at spaced apart locations therein and electrically connected to said first end of said first external conductor; and a second elongated contact blade formed with said distal connector ring receptacle contact and said second unipolar receptacle contact at spaced apart locations therein and electrically connected to said first end of said second external conductor, and said adaptor connector housing further comprises means for separating said first and second contact blades and for orienting said proximal connector pin receptacle contact and said distal connector ring receptacle contact at spaced apart locations along said elongated receptacle and for orienting said first unipolar receptacle contact with respect to said first unipolar receptacle and said second unipolar receptacle contact with respect to said second unipolar receptacle.

16. The external medical lead adaptor of claim 15, wherein said locking means further comprises:

spring means internal to said adaptor connector assembly coupled with a first end of said first and second elongated contact blades for biasing said proximal connector pin receptacle contact and said distal connector ring receptacle contact into said interference relationship with said elongated receptacle and said slot means in said normally closed position and for biasing said first and second unipolar receptacle contacts into an interference relationship with said first and second unipolar receptacles in said normally closed position; and a push-button extending through a wall of said adaptor connector assembly and coupled to second ends of said first and second elongated contact blades that may be depressed for moving said first and second elongated contact blades against said spring means and for thereby moving said proximal connector pin receptacle contact and said distal connector ring receptacle contact and said first and second unipolar receptacle contacts out of said interference relationship into said open position.

17. A method of making a rapid electrical connection using a medical lead adaptor between an external medical device connector terminal and a proximal lead connector end assembly of an implantable cardiac lead of the type having an elongated implantable lead body extending from the lead connector end assembly toward the distal cardiac lead end, the implantable lead body containing an implantable lead conductor coupled to a proximal lead connector element of the lead connector end assembly and having a lumen formed therein for receiving a stylet wire through a lumen end opening, whereby the stylet wire, when received in the lumen, extends proximally from the lumen end opening of the lead connector end assembly so that the stylet wire may be manipulated, the method comprising the steps of:

connecting the external medical device terminal with an external connector element of an external electrical conductor extending between a first external conductor end thereof to a second external conductor end formed with the external connector element; and attaching an adaptor connector assembly with the lead connector end assembly for making electrical contact between each respective implantable lead connector element and each external electrical conductor, the adaptor connector assembly having a proximal end wall and a distal end wall and side walls therebetween defining an adapter connector housing and further comprising the steps of:

unblocking axial and lateral slot access to an elongated receptacle extending from a proximal end opening to a distal end opening thereof in said proximal and distal end walls, the elongated receptacle shaped to conformably receive each lead connector element of the lead connector end assembly when inserted axially therein and having an elongated slot opening extending laterally of said elongated receptacle through a side wall of said adaptor connector assembly to an exterior surface thereof;

laterally inserting the stylet wire extending proximally from said lumen end opening of said lead connector end assembly through said laterally extending slot and into said elongated receptacle to position the stylet wire to extend proximally from said proximal end wall receptacle opening when said lead connector end assembly is axially inserted into said elongated receptacle;

axially inserting said lead connector end assembly into said elongated receptacle through said distal end wall receptacle opening in said distal end wall; and locking said lead connector end assembly in said elongated receptacle by applying an elongated receptacle contact electrically coupled with said first external electrical conductor against a lead connector element with force resisting withdrawal of said lead connector end assembly from said elongated receptacle and assuring secure electrical contact between said elongated receptacle contact and said lead connector element while allowing manipulation of the stylet wire with respect to said lumen.

18. The method of claim 17, wherein said unblocking step comprises moving said elongated receptacle contact from a normally closed position in an interference relationship with said elongated receptacle and said laterally extending slot to an open position allowing axial access through said distal end opening proximally through said elongated receptacle and lateral insertion of said stylet wire through said laterally extending slot into said elongated receptacle.

19. A method of making a rapid electrical connection using a medical lead adaptor between external medical device connector terminals and a proximal lead connector end assembly of an implantable bipolar cardiac lead of the type having an elongated implantable lead body extending from the lead connector end assembly toward the distal cardiac lead end, the implantable lead body containing first and second implantable lead conductors coupled to a proximal lead connector pin and a more distal connector ring, respectively, of the lead connector end assembly and having a lumen formed therein for receiving a stylet wire through a lumen end opening, whereby the stylet wire, when received in the lumen, extends proximally from the lumen end opening of the lead connector end assembly so that the stylet wire may be manipulated, the method comprising the steps of:

connecting the external medical device terminals with external connector elements of first and second external electrical conductors each extending between a first external conductor end thereof to a second external conductor end formed with the external connector element; and attaching an adaptor connector assembly with the lead connector end assembly for making electrical contact between the connector pin and ring and the first and second external electrical conductors, the adaptor connector assembly having a proximal end wall and a distal end wall and side walls therebetween defining an adapter connector housing and further comprising the steps of:

unblocking axial and lateral slot access to an elongated receptacle extending from a proximal end opening to a distal end opening thereof in said proximal and distal end walls, the elongated receptacle shaped to conformably receive the connector pin and ring of the lead connector end assembly when inserted axially therein and having an elongated slot opening extending laterally of said elongated receptacle through a side wall of said adaptor connector assembly to an exterior surface thereof;

laterally inserting the stylet wire extending proximally from said lumen end opening of said lead connector end assembly through said laterally extending slot and into said elongated receptacle to position the stylet wire to extend proximally from said proximal end wall receptacle opening when said lead connector end assembly is axially inserted into said elongated receptacle;

axially inserting said lead connector end assembly into said elongated receptacle through said distal end wall receptacle opening in said distal end wall; and locking said lead connector end assembly in said elongated receptacle by applying first and second elongated receptacle contacts electrically coupled with said first and second external electrical conductors against the lead connector pin and ring, respectively, with force resisting withdrawal of said lead connector end assembly from said elongated receptacle and assuring secure electrical contact between said elongated receptacle contacts and said lead connector pin and ring while allowing manipulation of the stylet wire with respect to said lumen.

20. The method of claim 19, wherein said unblocking step comprises moving said elongated receptacle contacts from a normally closed position in an interference relationship with said elongated receptacle and said laterally extending slot to an open position allowing axial access through said distal end opening proximally through said elongated receptacle and lateral insertion of said stylet wire through said laterally extending slot into said elongated receptacle.

21. A method of making a rapid electrical connection using a medical lead adaptor between a first external medical device connector terminal and the proximal lead connector pin of an indifferent electrode bearing lead and between a second external medical device terminal and the proximal lead connector pin of an implantable bipolar cardiac lead of the type having an elongated implantable lead body extending from a bipolar lead connector end assembly toward the distal cardiac lead end, the implantable lead body containing first and second implantable lead conductors coupled to the proximal lead connector pin and a more distal connector ring, respectively, of the lead connector end assembly and having a lumen formed therein for receiving a stylet wire through a lumen end opening, whereby the stylet wire, when received in the lumen, extends proximally from the lumen end opening of the lead connector end assembly so that the stylet wire may be manipulated, the method comprising the steps of:

connecting the external medical device terminals with external connector elements of first and second external electrical conductors each extending between a first external conductor end thereof to a second external conductor end formed with the external connector element; and attaching an adaptor connector assembly with the lead connector end assembly for making electrical contact between the respective proximal lead connector pin of the bipolar lead and the first external electrical conductor and between the proximal lead connector pin of the indifferent electrode bearing lead and the second external electrical conductor, the adaptor connector assembly having a proximal end wall and a distal end wall and side walls therebetween defining an adapter connector housing and further comprising the steps of:

unblocking axial and lateral slot access to an elongated bipolar receptacle extending from a proximal end opening to a distal end opening thereof in said proximal and distal end walls, the elongated bipolar receptacle shaped to conformably receive the connector pin and ring of the bipolar lead connector end assembly when inserted axially therein and having an elongated slot opening extending laterally of said elongated bipolar receptacle through a side wall of said adaptor connector assembly to an exterior surface thereof;

laterally inserting the stylet wire extending proximally from said lumen end opening of said lead connector end assembly through said laterally extending slot and into said elongated bipolar receptacle to position the stylet wire to extend proximally from said proximal end wall receptacle opening when said lead connector end assembly is axially inserted into said elongated bipolar receptacle;

axially inserting said bipolar lead connector end assembly into said elongated bipolar receptacle through said distal end wall receptacle opening in said distal end wall;

unblocking axial access to a unipolar receptacle extending from an end wall opening thereof in one of said proximal and distal end walls;

axially inserting said lead connector pin of said indifferent electrode bearing lead into said unipolar receptacle;

locking said bipolar lead connector end assembly in said elongated bipolar receptacle by applying a first elongated receptacle contact electrically coupled with said first external electrical conductor against the bipolar lead connector pin with force resisting withdrawal of said bipolar lead connector end assembly from said elongated bipolar receptacle and assuring secure electrical contact between said elongated bipolar receptacle contact and said bipolar lead connector pin while allowing manipulation of the stylet wire with respect to said lumen; and locking said unipolar lead connector end assembly in said unipolar receptacle by applying a unipolar receptacle contact electrically coupled with said second external electrical conductor against the unipolar lead connector pin with force resisting withdrawal of said unipolar lead connector end assembly from said unipolar receptacle and assuring secure electrical contact between said unipolar receptacle contact and said unipolar connector pin.

22. The method of claim 21 wherein said unblocking step comprises moving said unipolar and bipolar receptacle contacts from a normally closed position in an interference relationship with said unipolar receptacle and said elongated bipolar receptacle and said laterally extending slot to an open position allowing axial access through said end receptacle openings thereof and lateral insertion of said stylet wire through said laterally extending slot into said elongated receptacle.

23. A method of manufacturing an external medical lead adaptor for making a rapid electrical connection between an external medical device connector terminal and a proximal lead connector end assembly of an implantable cardiac lead of the type having an elongated implantable lead body extending from the lead connector end assembly toward the distal cardiac lead end, the implantable lead body containing an implantable lead conductor coupled to a proximal lead connector element of the lead connector end assembly and having a lumen formed therein for receiving a stylet wire through a lumen end opening, whereby the stylet wire, when received in the lumen, extends proximally from the lumen end opening of the lead connector end assembly so that the stylet wire may be manipulated, the method comprising:

forming external conductor means having at least one external electrical conductor therein extending between a first external conductor end thereof to a second external conductor end formed with an external connector element for making electrical contact with the external medical device connector terminal; and forming an adaptor connector assembly for receiving the lead connector end assembly and for making electrical contact between each respective implantable lead connector element and each external electrical conductor, the adaptor connector assembly having a proximal end wall and a distal end wall and side walls therebetween defining an adapter connector housing and further comprising the is steps of:

forming receiver means internal to the adaptor connector assembly defining an elongated receptacle extending from a proximal end opening to a distal end opening shaped to conformably receive each lead connector element of the lead connector end assembly when inserted axially therein;

locating elongated receptacle contact means along said elongated receptacle for making electrical contact with a lead connector element when inserted axially into the elongated receptacle;

electrically connecting said elongated receptacle contact means with said first external conductor end;

forming slot means extending laterally of said elongated receptacle through a side wall of said adaptor connector assembly to an exterior surface thereof for laterally receiving the stylet wire extending proximally from said lumen end opening of said lead connector end assembly to position the stylet wire to extend proximally from said proximal end wall when said lead connector end assembly is axially inserted into said elongated receptacle; and coupling locking means with said elongated receptacle contact means to be manipulatable from a normally closed position, blocking lateral insertion of said stylet wire through said slot means into said elongated receptacle and extending through said distal end wall and blocking axial insertion of said lead connector end assembly into said elongated receptacle, to an open position with respect to said slot means and said elongated receptacle, for allowing said stylet wire extending proximally from said lumen end opening to be inserted laterally through the slot means into the elongated receptacle and for then allowing the implantable lead connector end assembly to be axially inserted into a distal end opening of said elongated receptacle, and to a locked position, wherein said elongated receptacle contact means is applied against a lead connector element with force resisting withdrawal of said lead connector end assembly from said elongated receptacle and assuring secure electrical contact between said elongated receptacle contact means and said lead connector element while allowing manipulation of the stylet wire with respect to said lumen.

24. The manufacturing method of claim 23, further comprising:

providing spring means internal to said adaptor connector assembly coupled with said elongated receptacle contact means for biasing said elongated receptacle contact means into said interference relationship; and providing a push-button extending through a wall of said adaptor connector assembly and coupled to said elongated receptacle contact means that is manipulatable for moving said elongated receptacle contact means against said spring means and out of said interference relationship into said open position.

25. The manufacturing method of claim 23, wherein said implantable cardiac lead comprises a bipolar cardiac lead having an elongated, in-line, lead connector end assembly formed with a proximal connector pin and a more distal connector ring and further comprising:

configuring said elongated receptacle to receive said elongated bipolar, inline lead connector end assembly;

providing a proximal connector pin receptacle contact and a more distal connector ring receptacle contact as said elongated receptacle contact means;

providing first and second external electrical conductors in said external conductor means each extending between a first external conductor end thereof to a second external conductor end thereof formed with an external connector element for making electrical contact with the external medical device connector terminal;

coupling said proximal connector pin receptacle contact with said first external conductor end of said first external electrical conductor; and coupling said connector ring receptacle contact with said first external conductor end of said second external electrical conductor.

26. The manufacturing method of claim 25, further comprising the step of forming said elongated receptacle contact means to be movable with respect to said elongated receptacle to dispose said proximal connector pin receptacle contact and distal connector ring receptacle contact into interference relationship with said elongated receptacle and said slot means in said normally closed position.

27. The manufacturing method of claim 26, wherein said locking step further comprises:

providing spring means internal to said adaptor connector assembly coupled with said elongated receptacle contact means for biasing said proximal connector pin receptacle contact and said distal connector ring receptacle contact into said interference relationship with said elongated receptacle and said slot means in said normally closed position; and providing a push-button extending through a wall of said adaptor connector assembly and coupled to said proximal connector pin receptacle contact and distal connector ring receptacle contact that is manipulatable for moving said proximal connector pin receptacle contact and said distal connector ring receptacle contact against said spring means and out of said interference relationship into said open position.

28. The manufacturing method of claim 27, wherein said receiver means further comprises first and second, spaced apart, unipolar receptacles for receiving unipolar lead connector pins of first and second unipolar implantable cardiac leads, and further comprising the steps of:

positioning a first unipolar receptacle contact along said first unipolar receptacle for making electrical contact with a first unipolar lead connector element when inserted axially into said first unipolar receptacle; and positioning a second unipolar receptacle contact along said second unipolar receptacle for making electrical contact with a second unipolar lead connector element when inserted axially into said second unipolar receptacle.

29. The manufacturing method of claim 28, wherein said electrically connecting step comprises:

coupling said first unipolar receptacle contact with said first external conductor end of said first external electrical conductor; and coupling said second unipolar receptacle contact with said first external conductor end of said second external electrical conductor.

30. The manufacturing method of claim 25 further comprising the steps of:

providing first and second, spaced apart, unipolar receptacles in said adaptor connector assembly for receiving unipolar lead connector pins of first and second unipolar implantable cardiac leads;

positioning a first unipolar receptacle contact along said first unipolar receptacle for making electrical contact with a first unipolar lead connector element when inserted axially into said first unipolar receptacle; and positioning a second unipolar receptacle contact along said second unipolar receptacle for making electrical contact with a second unipolar lead connector element when inserted axially into said second unipolar receptacle.

31. The manufacturing method of claim 30, wherein said electrically connecting step further comprises coupling said first unipolar receptacle contact with said first external conductor end of said first external electrical conductor; and coupling said second unipolar receptacle contact with said first external conductor end of said second external electrical conductor.

32. The manufacturing method of claim 31, further comprising the steps of:

providing a first elongated contact blade formed with said proximal connector pin receptacle contact and said first unipolar receptacle contact at spaced apart locations therein and electrically connected to said first end of said first external conductor; and providing a second elongated contact blade formed with said distal connector ring receptacle contact and said second unipolar receptacle contact at spaced apart locations therein and electrically connected to said first end of said second external conductor, and separating said first and second contact blades from one another and orienting said proximal connector pin receptacle contact and said distal connector ring receptacle contact at spaced apart locations along said elongated receptacle and for orienting said first unipolar receptacle contact with respect to said first unipolar receptacle and said second unipolar receptacle contact with respect to said second unipolar receptacle.

33. The manufacturing method of claim 32, wherein said step of forming locking means further comprises:

arranging spring means internal to said adaptor connector assembly coupled with a first end of said first and second elongated contact blades for biasing said proximal connector pin receptacle contact and said distal connector ring receptacle contact into said interference relationship with said elongated receptacle and said slot means in said normally closed position and for biasing said first and second unipolar receptacle contacts into an interference relationship with said first and second unipolar receptacles in said normally closed position; and arranging a push-button extending through a wall of said adaptor connector assembly and coupled to second ends of said first and second elongated contact blades that may be depressed for moving said first and second elongated contact blades against said spring means and for thereby moving said proximal connector pin receptacle contact and said distal connector ring receptacle contact and said first and second unipolar receptacle contacts out of said interference relationship into said open position.

* * * * *